(12) United States Patent
Thomas et al.

(10) Patent No.: US 11,369,400 B2
(45) Date of Patent: Jun. 28, 2022

(54) BALLOON DISSECTOR

(71) Applicant: Covidien LP, Mansfield, MA (US)

(72) Inventors: Jonathan Thomas, New Haven, CT (US); Jay Breindel, Kensington, CT (US)

(73) Assignee: Covidien LP, Mansfield, MA (US)

( * ) Notice: Subject to any disclaimer, the term of this patent is extended or adjusted under 35 U.S.C. 154(b) by 120 days.

(21) Appl. No.: 16/358,866

(22) Filed: Mar. 20, 2019

(65) Prior Publication Data

US 2020/0297371 A1 Sep. 24, 2020

(51) Int. Cl.
| | |
|---|---|
| *A61B 17/32* | (2006.01) |
| *A61B 17/02* | (2006.01) |
| *A61M 25/10* | (2013.01) |
| *A61B 17/00* | (2006.01) |
| *A61M 29/02* | (2006.01) |

(52) U.S. Cl.
CPC .......... *A61B 17/32* (2013.01); *A61B 17/0218* (2013.01); *A61M 25/1018* (2013.01); *A61B 2017/00557* (2013.01); *A61B 2017/320048* (2013.01); *A61M 29/02* (2013.01)

(58) Field of Classification Search
CPC ........ A61B 17/32; A61B 2017/320048; A61B 2017/320044; A61B 17/0218; A61B 2017/00557; A61M 25/1018; A61M 2025/1072; A61M 2025/1059; A61M 29/02; A61M 25/10
See application file for complete search history.

(56) References Cited

U.S. PATENT DOCUMENTS

| | | |
|---|---|---|
| 397,060 A | 1/1889 | Knapp |
| 512,456 A | 1/1894 | Sadikova |
| 1,213,005 A | 1/1917 | Pillsbury |
| 2,912,981 A | 11/1959 | Keough |
| 2,936,760 A | 5/1960 | Gains |
| 3,039,468 A | 6/1962 | Price |

(Continued)

FOREIGN PATENT DOCUMENTS

| | | |
|---|---|---|
| CA | 2345056 A1 | 2/2001 |
| DE | 10254503 A1 | 6/2004 |

(Continued)

OTHER PUBLICATIONS

European Search Report dated Jul. 1, 2020, issued in EP Appln. No. 20164312, 10 pages.

*Primary Examiner* — Diane D Yabut
*Assistant Examiner* — Brigid K Byrd
(74) *Attorney, Agent, or Firm* — Carter, DeLuca & Farrell LLP

(57) ABSTRACT

A balloon dissector assembly includes a balloon dissector having an elongate shaft, a handle disposed on a proximal portion of the elongate shaft, and a dissection balloon supported on a distal portion of the elongate shaft. The dissection balloon includes a substantially cylindrical shape having a deflated condition in which the dissection balloon includes a first diameter between the proximal and distal ends, an inflated condition in which the dissection balloon includes a second diameter between the proximal and distal ends, and a plurality of intermediate conditions in which the balloon transitions from the deflated condition to the inflated condition progressively from the proximal end to the distal end.

19 Claims, 4 Drawing Sheets

(56) References Cited

U.S. PATENT DOCUMENTS

| | | | |
|---|---|---|---|
| 3,050,066 A | 8/1962 | Koehn |
| 3,168,092 A | 2/1965 | Silverman |
| 3,253,594 A | 5/1966 | Matthews et al. |
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,479,497 A | 10/1984 | Fogarty et al. |
| 4,485,805 A | 12/1984 | Foster, Jr. |
| 4,490,137 A | 12/1984 | Moukheibir |
| 4,496,345 A | 1/1985 | Hasson |
| 4,526,175 A | 7/1985 | Chin et al. |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,946,440 A | 8/1990 | Hall |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,391,178 A | 2/1995 | Yaper |
| 5,397,311 A | 3/1995 | Walker et al. |
| 5,402,772 A | 4/1995 | Moll et al. |
| 5,407,433 A | 4/1995 | Loomas |
| 5,425,357 A | 6/1995 | Moll et al. |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,545,209 A * | 8/1996 | Roberts ............... A61F 2/958 |
| | | 604/103.05 |
| 5,601,589 A * | 2/1997 | Fogarty ............ A61B 17/00008 |
| | | 600/207 |
| 5,607,441 A * | 3/1997 | Sierocuk ............ A61B 17/0218 |
| | | 600/207 |
| 5,607,443 A * | 3/1997 | Kieturakis ......... A61B 17/0218 |
| | | 600/207 |
| 5,632,761 A | 5/1997 | Smith et al. |
| 5,656,013 A | 8/1997 | Yoon |
| 5,667,479 A | 9/1997 | Kieturakis |
| 5,667,480 A | 9/1997 | Knight et al. |
| 5,667,520 A | 9/1997 | Bonutti |
| 5,690,668 A | 11/1997 | Fogarty et al. |
| 5,695,514 A | 12/1997 | Chin |
| 5,702,416 A | 12/1997 | Kieturakis et al. |
| 5,704,372 A | 1/1998 | Moll et al. |
| 5,707,382 A | 1/1998 | Sierocuk et al. |
| 5,713,869 A | 2/1998 | Morejon |
| 5,720,762 A * | 2/1998 | Bass ................. A61B 17/0218 |
| | | 606/192 |
| 5,722,934 A | 3/1998 | Knight et al. |
| 5,722,986 A | 3/1998 | Smith et al. |
| 5,725,545 A | 3/1998 | Bircoll |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,814,059 A | 9/1998 | Hart et al. |
| 5,814,060 A | 9/1998 | Fogarty et al. |
| 5,836,913 A | 11/1998 | Orth et al. |

(56) References Cited

U.S. PATENT DOCUMENTS

| | | |
|---|---|---|
| 5,836,961 A | 11/1998 | Kieturakis et al. |
| RE36,043 E | 1/1999 | Knighton |
| 5,865,802 A | 2/1999 | Yoon et al. |
| 5,873,889 A | 2/1999 | Chin |
| 5,893,866 A | 4/1999 | Hermann et al. |
| 5,902,316 A | 5/1999 | Mollenauer |
| 5,904,699 A | 5/1999 | Schwemberger et al. |
| 5,925,058 A | 7/1999 | Smith et al. |
| 5,944,734 A | 8/1999 | Hermann et al. |
| 5,951,584 A | 9/1999 | Hermann |
| 5,968,066 A | 10/1999 | Fogarty et al. |
| 5,979,452 A | 11/1999 | Fogarty et al. |
| 6,013,090 A | 1/2000 | Fogarty et al. |
| 6,015,421 A | 1/2000 | Echeverry et al. |
| 6,036,714 A | 3/2000 | Chin |
| 6,102,928 A | 8/2000 | Bonutti |
| 6,152,895 A | 11/2000 | Wilk |
| 6,168,608 B1 | 1/2001 | Echeverry et al. |
| 6,277,136 B1 | 8/2001 | Bonutti |
| 6,312,442 B1 | 11/2001 | Kieturakis et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,436,118 B1* | 8/2002 | Kayan ............... A61B 17/00008 606/190 |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,592,602 B1 | 7/2003 | Peartree et al. |
| 7,037,317 B2 | 5/2006 | Hermann et al. |
| 7,300,448 B2 | 11/2007 | Criscuolo et al. |
| 7,311,719 B2 | 12/2007 | Bonutti |
| 7,744,617 B2 | 6/2010 | Lunsford et al. |
| 7,938,842 B1 | 5/2011 | Chin |
| 7,963,975 B2 | 6/2011 | Criscuolo |
| 8,454,645 B2 | 6/2013 | Criscuolo et al. |
| 8,500,770 B2 | 8/2013 | Echevery et al. |
| 8,540,745 B2 | 9/2013 | Criscuolo et al. |
| 10,070,853 B2 | 9/2018 | Gould |
| 2003/0004529 A1 | 1/2003 | Tsonton et al. |
| 2004/0243167 A1 | 12/2004 | Tanaka et al. |
| 2005/0004592 A1* | 1/2005 | Criscuolo .......... A61B 17/0218 606/190 |
| 2005/0165437 A1 | 7/2005 | Takimoto |
| 2005/0261724 A1* | 11/2005 | Bacher ............... A61B 17/0218 606/192 |
| 2007/0028923 A1 | 2/2007 | Souris et al. |
| 2007/0078477 A1 | 4/2007 | Heneveld et al. |
| 2007/0250104 A1* | 10/2007 | Condrea ................ A61M 29/02 606/193 |
| 2009/0182368 A1 | 7/2009 | Lunsford et al. |
| 2010/0041951 A1* | 2/2010 | Glozman .......... A61M 25/0155 600/115 |
| 2010/0305602 A1 | 12/2010 | Hermann et al. |
| 2012/0203220 A1 | 8/2012 | Brannan et al. |
| 2012/0259375 A1 | 10/2012 | Druma et al. |
| 2012/0303018 A1 | 11/2012 | Ladtkow et al. |
| 2013/0023733 A1 | 1/2013 | Worrel et al. |
| 2013/0046332 A1 | 2/2013 | Jones et al. |
| 2013/0060273 A1 | 3/2013 | Fogarty et al. |
| 2013/0110151 A1 | 5/2013 | Criscuolo et al. |
| 2014/0214057 A1* | 7/2014 | Piccagli ................ A61B 17/32 606/159 |
| 2014/0277069 A1* | 9/2014 | Bhagchandani .. A61M 25/1027 606/194 |
| 2014/0330074 A1* | 11/2014 | Morriss ............. A61M 25/0041 600/104 |
| 2015/0051631 A1 | 2/2015 | Gould |
| 2017/0135715 A1 | 5/2017 | Breindel et al. |
| 2018/0140812 A1* | 5/2018 | Onishi .................. A61M 29/02 |

FOREIGN PATENT DOCUMENTS

| | | |
|---|---|---|
| EP | 0480653 A1 | 4/1992 |
| EP | 0573273 A2 | 12/1993 |
| EP | 0610099 A2 | 8/1994 |
| EP | 0880939 A1 | 12/1998 |
| GB | 2397023 A | 7/2004 |
| JP | 2008067994 A | 3/2008 |
| JP | 4144572 B2 | 9/2008 |
| WO | 8200408 A1 | 2/1982 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9324172 A1 | 12/1993 |
| WO | 9713464 A2 | 4/1997 |
| WO | 9721461 A1 | 6/1997 |
| WO | 9838920 A1 | 9/1998 |
| WO | 9912602 A1 | 3/1999 |
| WO | 0126724 A2 | 4/2001 |
| WO | 02096307 A2 | 12/2002 |
| WO | 2004032756 A2 | 4/2004 |
| WO | 2011128622 A2 | 10/2011 |
| WO | 2012004739 A2 | 1/2012 |
| WO | 2012047939 A2 | 4/2012 |
| WO | 2014030078 A1 | 2/2014 |

* cited by examiner

BALLOON DISSECTOR

BACKGROUND

Technical Field

The present disclosure relates to an apparatus and method for creating an anatomical space, and more particularly to an apparatus and method for creating an anatomical space with an elongate balloon that progressively inflates along its length.

Background of Related Art

There has been a growing trend in the use of surgical techniques to surgically close ventral defects by closing the midline fascia without creating tension in the abdominal wall. Simply bridging a defect with mesh is often not cosmetically appealing and often results in rectus diastasis. Midline closure without some form of component release leads to excessive lateral tension. The release of lateral components allows a surgeon to approximate the sides of a defect without generating tension. Traditionally, this method has been performed in an open approach. Dissection balloons allow this technique to be performed in a minimally invasive approach.

Traditional balloon dissectors use a round, or oblong balloon that is inflated from a collapsed condition to an expanded condition all at once along a length of the balloon. It would be beneficial to have a balloon dissector that inflates progressively along its length.

SUMMARY

A balloon dissector having an elongate balloon that progressively inflates along its length is provided. A balloon dissector assembly includes a balloon dissector having an elongate shaft, a handle disposed on a proximal portion of the elongate shaft, and a dissection balloon supported on a distal portion of the elongate shaft. The dissection balloon may have a substantially cylindrical shape having a deflated condition in which the dissection balloon has a first diameter between the proximal and distal ends, an inflated condition in which the dissection balloon has a second diameter between the proximal and distal ends, and a plurality of intermediate conditions in which the balloon transitions from the deflated condition to the inflated condition progressively from the proximal end to the distal end.

In embodiments, the dissector assembly further includes a guide assembly selectively engageable with the balloon dissector. The guide assembly may include a housing and a guide member extending from the housing.

In some embodiments, the second diameter of the dissection balloon is greater than the first diameter of the dissection balloon. The dissection balloon may have a first length when the dissection balloon is in the deflated condition and a second length when the dissection balloon is in the inflated condition. The second length may be greater than the first length. The housing of the guide assembly may be configured for snap-fit engagement with the handle of the balloon dissector. The handle of the balloon dissector may include an inflation port. The dissection balloon may be transparent.

The dissector assembly may further include an access assembly configured to releasably receive the balloon dissector assembly.

Also provided is a method for separating tissue. The method includes directing a dissection balloon through tissue of a patient. The dissection balloon may have proximal and distal portions and define a longitudinal axis. The method further includes providing inflation fluid to the dissection balloon to inflate the dissection balloon progressively along the longitudinal axis from the proximal portion to the distal portion. Directing the dissection balloon through tissue of patient may include receiving a guide member of a guide assembly through the dissection balloon.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
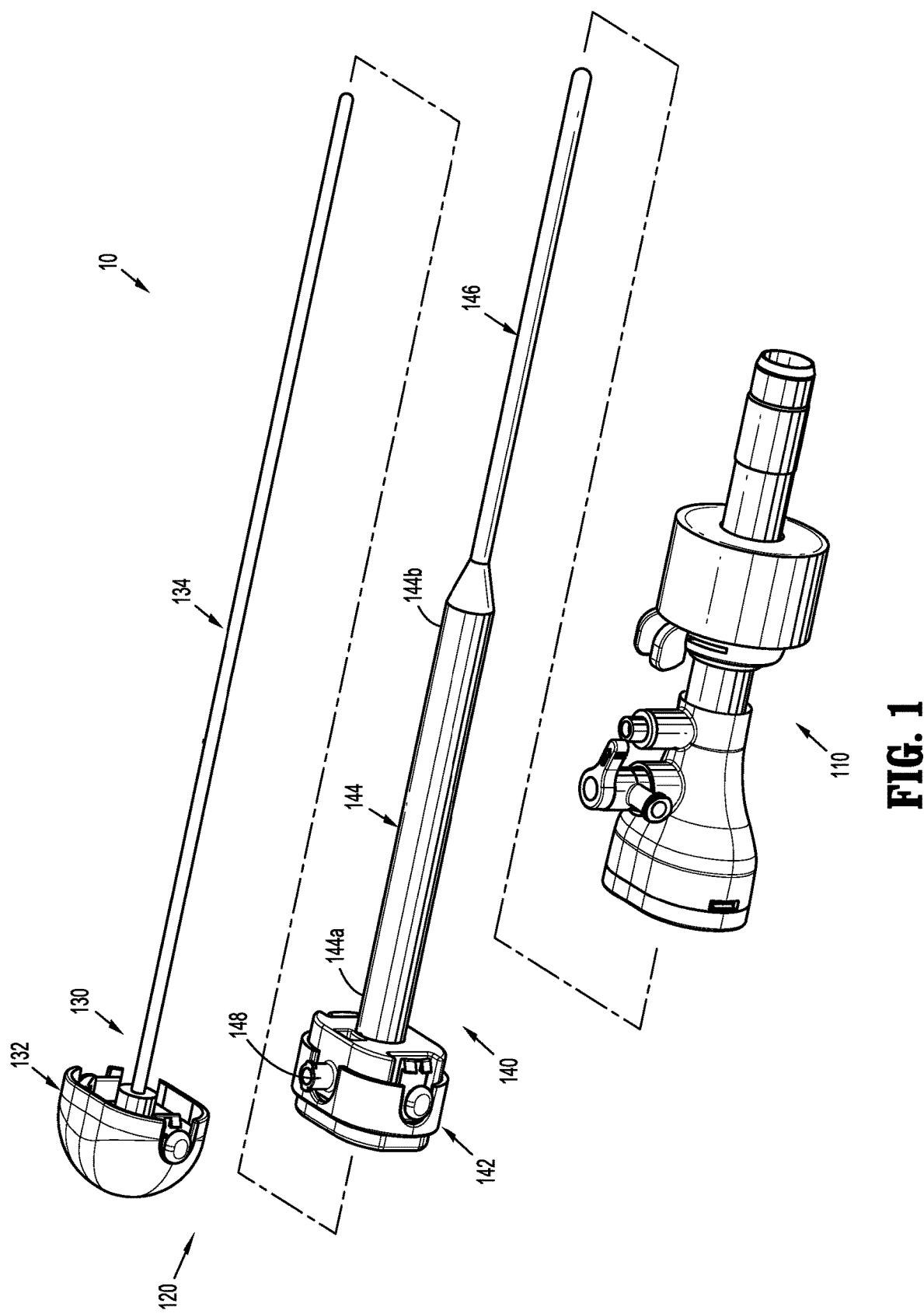
FIG. 1 is a perspective view of a dissector assembly according to the present disclosure including an access assembly and a balloon dissection assembly.

Referring now to the drawings wherein like reference numerals illustrate similar components throughout the several views, there are illustrated embodiments of access assemblies according the principles of the present disclosure. As shown in the drawings and as described throughout the following description, as is traditional when referring to relative positioning on an object, the term "proximal" refers to the end of the apparatus which is closer to the user and the term "distal" refers to the end of the apparatus which is farther from the user.

Referring to FIG. 1, a dissection and access assembly according to an embodiment of the present disclosure is shown generally as dissector assembly 10. The dissector assembly 10 includes an access assembly 110 and a balloon dissector assembly 120.

Figure 6:
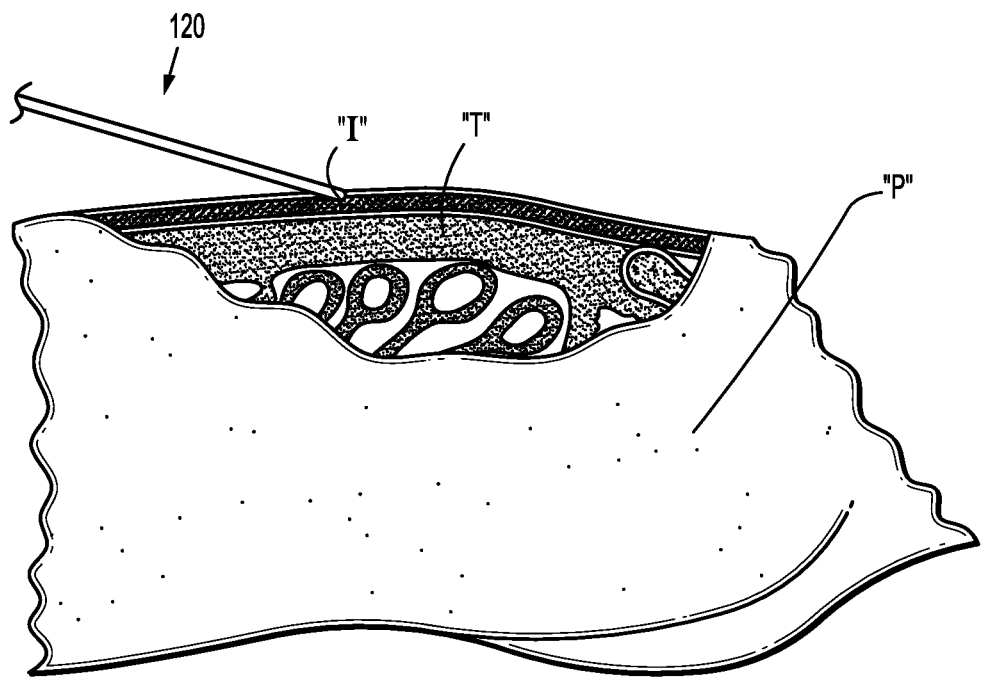
FIG. 6 is a schematic view of the balloon dissection assembly shown in FIG. 1, prior to insertion into an incision of a patient.

The access assembly 110 of the dissector assembly 10 provides sealed access to an anatomical space within a patient "P" (FIG. 6). For a detailed description of the structure and function of exemplary access assemblies, please refer to commonly owned U.S. Pat. No. 6,015,421 ("the '421 patent") and U.S. Pat. No. 7,300,448 ("the '448 patent"), the contents of which are incorporated herein by reference in their entireties.

With continue reference to FIG. 1, the balloon dissector assembly 120 of the dissector assembly 10 includes a guide assembly 130 and a balloon assembly 140. As will be described in further detail below, during operation, the guide assembly 130 is secured to the balloon assembly 140, and the combination is received though the access assembly 110 to create an anatomical space within a patient "P" (FIG. 6).

The guide assembly 130 and the balloon assembly 140 of the balloon dissector assembly 120 will only be described to the extent necessary to fully disclose the aspects of the present disclose. For a detailed description of the structure and function of an exemplary balloon dissector assembly including exemplary guide and balloon assemblies, please refer to the '421 and '448 patents, the contents of which were previously incorporated herein.

The guide assembly 130 of the balloon dissector assembly 120 of the dissector assembly 110 includes a housing 132 and a guide member 134 extending distally from the housing 132. The housing 132 is configured for snap-fit engagement with the balloon assembly 132 and is configured for operable engagement by a user. The guide member 134 of the guide assembly 130 may be formed of metal, plastic, or other suitable material. In embodiments, the guide member 134 is flexible, and/or may include one or more lumens. The guide assembly 130 may include an articulation mechanism (not shown) for articulating the guide member 134 to facilitate placement of the guide member 134 through tissue "T". The guide assembly 130 may support a scope or other means for viewing the tissue through which the guide member 134 is inserted.

With continued reference to FIG. 1, the balloon assembly 140 of the balloon dissector assembly 120 includes a handle 142, an elongate shaft 144, and a dissection balloon 146. The handle 142 of the balloon assembly 140 is configured for snap-fit engagement with the access assembly 110 when the balloon assembly 140 is received through the access assembly 110. As noted above, the balloon assembly 140 is also configured for snap-fit engagement with the guide assembly 130. More particularly, the housing 132 of the guide assembly 130 is configured for snap-fit engagement with the handle 142 of the balloon assembly 140.

The handle 142 of the balloon assembly 140 may include a port 148 or be otherwise configured for operable connection to a source of inflation fluid, e.g., air, saline, etc. The handle 142 of the balloon assembly 140 is secured to a proximal portion 144a of the elongate shaft 144. The dissection balloon 146 is secured to a distal portion 144b of the elongate shaft 144.

With additional reference to FIGS. 2-5, the dissection balloon 146 of the balloon assembly 140 is formed of an elastic material, e.g., rubber, latex, or other suitable elastic material. In embodiments, the dissection balloon 146 is transparent, or translucent, or becomes transparent or translucent as the dissection balloon 146 is stretched over the guide member 134 of the guide assembly 130 and the material forming the dissection balloon 146 thins out. It is further envisioned that only a portion or portions of the dissection balloon 146 are transparent.

The dissection balloon 146 of the balloon assembly 140 of the balloon dissector assembly 120 includes a substantially cylindrical shape having a first diameter "d" (FIG. 3) when in a first or deflated condition and a second, maximum diameter "D" (FIG. 3) when in a second or inflated condition. The dissection balloon 146 includes a first length "l" (FIG. 2) when in the dissection balloon 146 is in the first or deflated condition and the dissection balloon 146 has a second length "L" (FIG. 5) when the dissection balloon 146 is in the second or inflated condition. In embodiments, the first length "l" of the dissection balloon 146 is less than the second length "L" of the dissection balloon 146.

Figure 2:
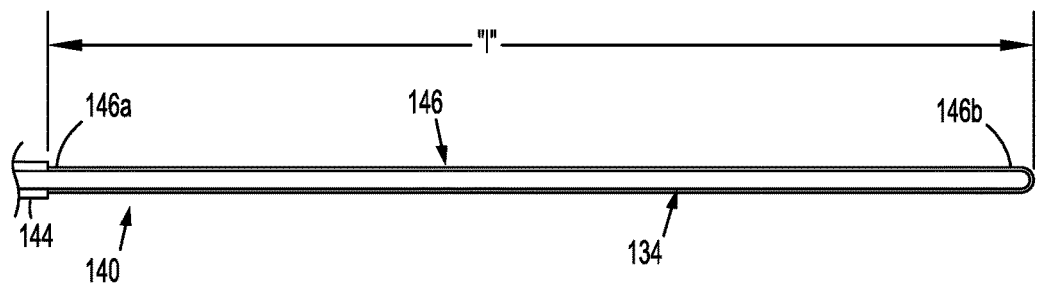
FIG. 2 is side view of a distal end of the balloon dissection assembly shown in FIG. 1, with the dissection balloon in a first or deflated condition.

As seen in FIG. 2, the guide member 134 of the guide assembly 130 is received through the handle 142 of the balloon assembly 140 and within the dissection balloon 146 of the balloon assembly 140, resulting in the dissection balloon 146 appearing rigid. When the guide member 134 is removed from within the dissection balloon 146 when the dissection balloon 146 is in the deflated condition by separating the guide assembly 130 and the balloon assembly 140, the dissection balloon 146 becomes flaccid.

The dissection balloon 146 of the balloon assembly 140 may be configured for loose reception about the guide member 134 of the guide assembly 130. Alternatively, the dissection balloon 146 may configured such that the dissection balloon 146 is stretched to accommodate the guide member 134 as the guide member 134 is received within the dissection balloon 146.

Figure 3:
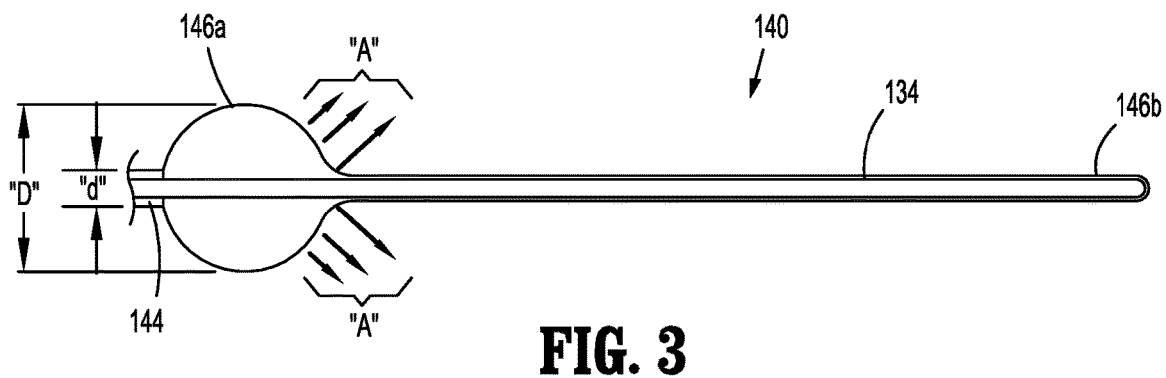
FIG. 3 is side view of the distal end of the balloon dissection assembly shown in FIG. 2, with the dissection balloon in a first partially inflated condition.

With particular reference now to FIGS. 2-5, the dissection balloon 146 of the balloon assembly 140 of the dissector assembly 10 is shown in progressive states of inflation. Referring initially to FIG. 2, the dissection balloon 146 of the balloon assembly 140 is shown in the first or deflated condition. As shown, the guide member 134 of the guide assembly 130 is received within the dissection balloon 146 of the balloon assembly 140, thereby giving the dissection balloon 146 the appearance of being rigid. As noted above, in the deflated condition, the dissection balloon 146 includes the first diameter "d" (FIG. 3).

The dissection balloon 146 of the balloon assembly 140 may be secured to the guide member 134 of the guide assembly 130 with adhesive. In this manner, the adhesive configured to release the dissection balloon 146 as the dissection balloon 146 is inflated. In embodiments, receipt of the dissection balloon 146 about the guide member 134 is sufficient to secure the dissection balloon 146 to the guide member 134 without adhesive. In other embodiments, the stretching of the dissection balloon 146 about the guide member 134 secures the dissection balloon 146 relative to the guide member 134.

Figure 4:
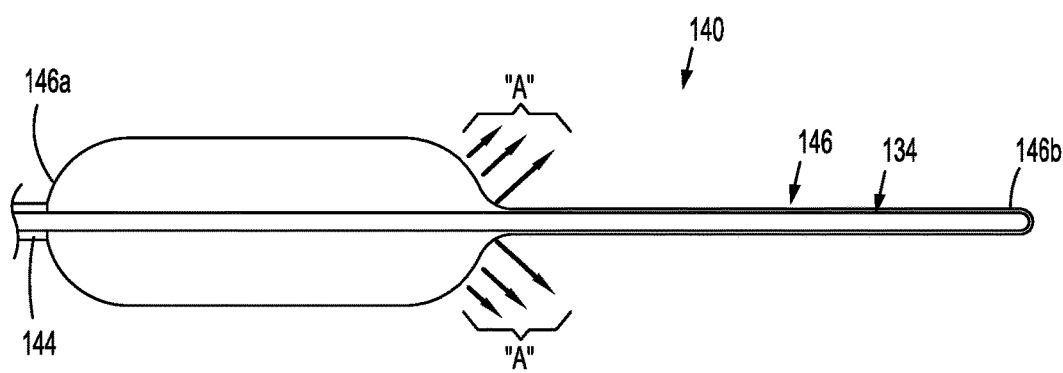
FIG. 4 is side view of the distal end of the balloon dissection assembly shown in FIGS. 2 and 3, with the dissection balloon in a second partially inflated condition.

Turning to FIGS. 3 and 4, an inflation fluid, e.g., air, saline, etc., is supplied to the dissection balloon 146 of the balloon assembly 140, the dissection balloon 146 inflates outwardly and progressively from a proximal portion 146a to a distal portion 146b, as indicated by arrows "B" shown in FIGS. 3 and 4. In this manner, the dissection balloon 146 inflates progressively along its length. As will be described in further detail below, the progressive inflation of the dissection balloon 146 allows for more controlled placement and inflation of the dissection balloon 146 to effect tissue separation and creation of an anatomical space.

Although the dissection balloon 146 of the balloon assembly 140 is shown and described as being progressively inflatable along its length from a proximal end to a distal end, it is envisioned that the balloon assembly 140 may be configured such that the dissection balloon 146 is inflated along its length from its distal end to its proximal end. Alternatively, it is envisioned that the dissection balloon 146 may be configured for inflation from a central portion of the dissection balloon 146 in first and second, e.g., proximal and distal, directions such that the balloon assembly 140 inflates progressively along its length from its middle outward.

Figure 5:
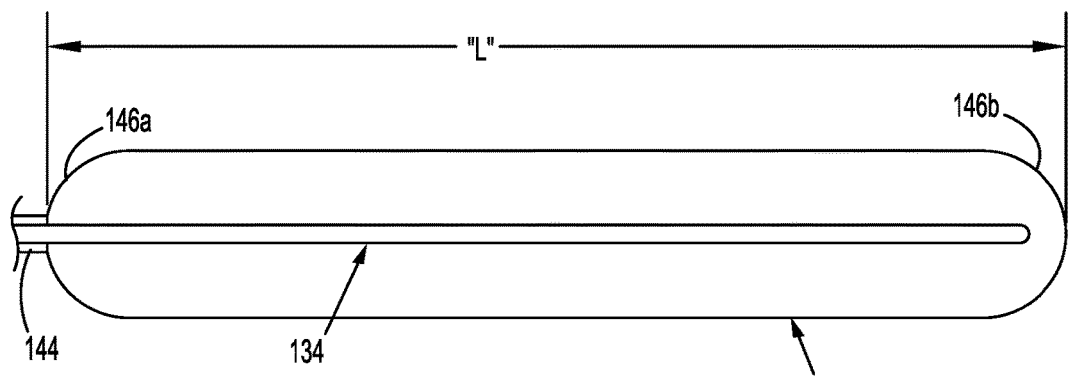
FIG. 5 is side view of the distal end of the balloon dissection assembly shown in FIGS. 2-4, with the dissection balloon in a fully inflated condition.

With reference to FIG. 5, when fully inflated, the dissection balloon 146 of the balloon assembly 140 includes a substantially cylindrical shape. The cylindrical shape of the dissection balloon 146 reduces the chances of perforating blood vessels during tissue separation. As noted above, the length and maximum diameter of the fully inflated dissection balloon 146 may be determined based on the desired dimensions of the anatomical space being created.

The dissector assembly 10 may be provided as a kit with various balloon assemblies having dissection balloons 146 of varying lengths and/or maximum diameters. In this manner, a clinician may choose a balloon assembly 140 having a dissection balloon 146 suitable for a given procedure.

The operation of the balloon dissector assembly 120 will now be described with reference now to FIGS. 6-9. Referring initially to FIG. 6, an incision "I" is first created in a patient "P" for accessing the underlying tissue, e.g., abdominal wall. The guide member 134 of the guide assembly 130, having been secured to the balloon dissector 140, is then inserted through the incision "I" and into the tissue "T". As noted above, the guide assembly 130 and the balloon dissector 140 may be provided as a kit with multiple balloon dissectors 140 having dissection balloons of various lengths and/or maximum diameters. Although shown and described as being directly inserted into the incision "I", the clinician may use an access assembly, e.g., the access assembly 110 to create a sealed port for accessing the tissue "T" of the patient "P".

Figure 7:
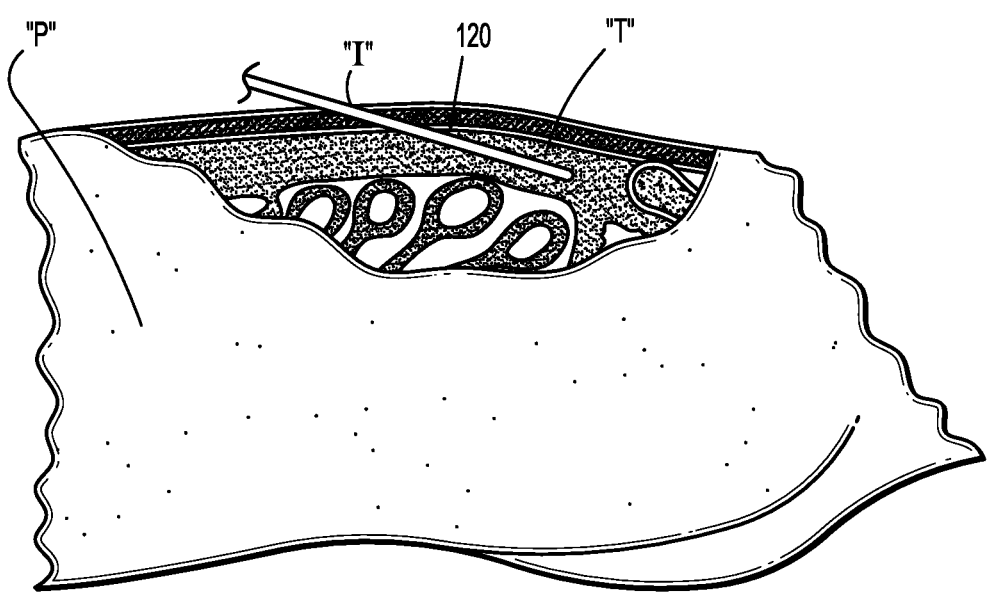
FIG. 7 is a schematic view of the balloon dissection assembly shown in FIG. 1, fully inserted in the patient and prior to inflation of the dissection balloon.

Turning to FIG. 7, the guide member 134 of the guide assembly 130, and the dissection balloon 146 through which the guide member 134 is received are then directed through the tissue "T". As noted above, the dissection balloon 146 may be transparent and the guide assembly 130 may include a scope or other means for viewing a distal end of the guide member 134 to facilitate directing of the guide member 134 between tissue layers. Alternatively, or in addition, insertion of the guide member 134 and dissection balloon 146 may be facilitated by x-ray, MM, or other imaging techniques. As also noted above, the guide assembly 130 may include an articulation mechanism (not shown) for articulating the guide member 134 during insertion to facilitate placement of the guide member 134 within the tissue "T". In embodiments, the guide member 134 is flexible to follow a natural path through tissue, e.g., between tissue layers.

Figure 8:
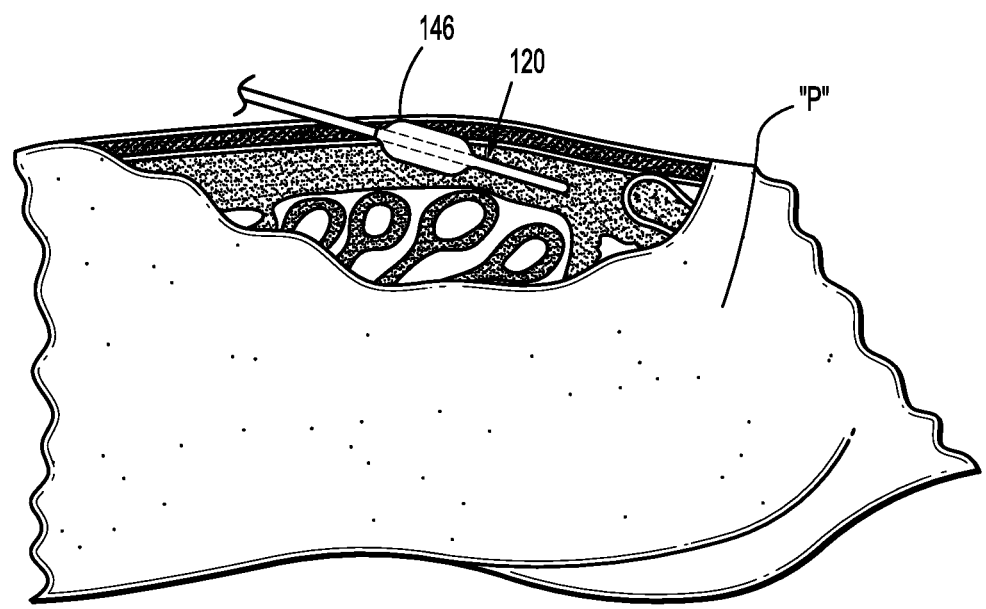
FIG. 8 is a schematic view of the balloon dissection assembly shown in FIG. 1, fully inserted in the patient and with the dissection balloon in a partially inflated condition.
Figure 9:
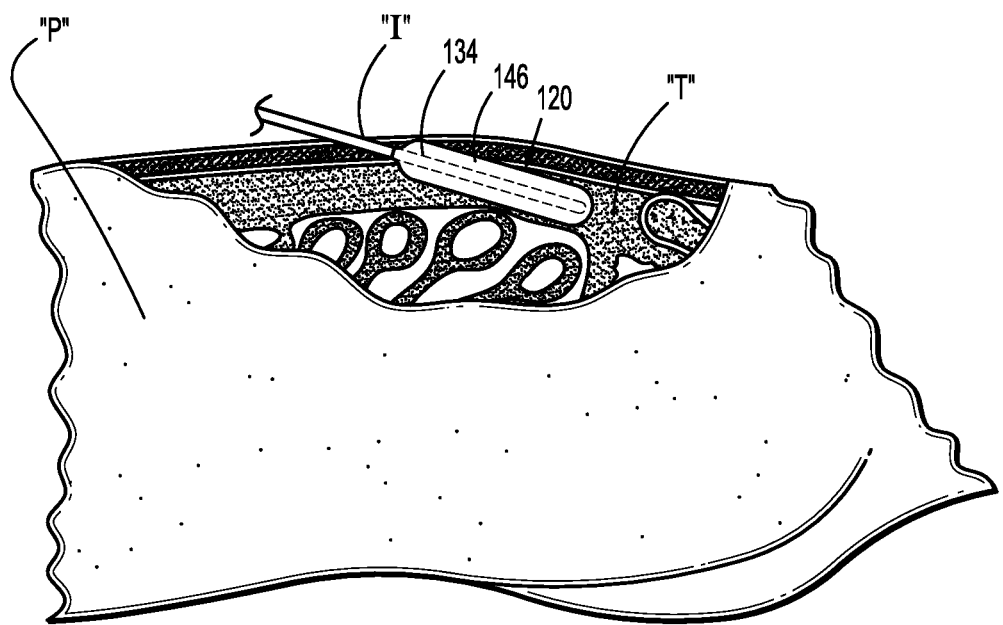
FIG. 9 is a schematic view of the balloon dissection assembly shown in FIG. 1, fully inserted in the patient and with the dissection balloon in a fully inflated condition.

With reference to FIGS. 8 and 9, once the guide member 134 of the guide assembly 130 is properly positioned within the tissue "T", inflation fluid is supplied to the dissection balloon 146 of the balloon dissector 140 in a controlled manner to cause the progressive inflation of the dissection balloon 146 along its length. The dissection balloon 146 inflates along its length from its proximal end to its distal end. As the dissection balloon 146 is inflated, the guide member 134 may be manipulated to more properly position the dissection balloon 146 within the tissue "T".

Once an anatomical space is created within the tissue "T" of the patient "P", the dissection balloon 146 of the balloon assembly 140 is deflated and the guide member 134 and dissection balloon 146 of the dissector assembly 120 are removed from the tissue "T" and the surgical procedure may be completed in a traditional manner.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described.

What is claimed is:

1. A balloon dissector assembly comprising:
    a balloon dissector including,
        an elongate shaft having a proximal portion and a distal portion and defining a longitudinal axis,
        a handle disposed on the proximal portion of the elongate shaft,
        a dissection balloon supported on the distal portion of the elongate shaft, the dissection balloon having proximal and distal ends and defining a length extending from the proximal end to the distal end; and
        a guide member extending through the elongate shaft and within the dissection balloon along the length of the dissection balloon, the dissection balloon including a substantially cylindrical shape having a deflated condition in which the dissection balloon extends distally from the distal portion of the elongate shaft and includes a first diameter between the proximal and distal ends, an inflated condition in which the dissection balloon is disposed about the distal portion of the elongate shaft and includes a second diameter between the proximal and distal ends, and a plurality of intermediate conditions in which the dissection balloon transitions from the deflated condition to the inflated condition progressively along the length of the dissection balloon from the proximal end of the dissection balloon to the distal end of the dissection balloon.

2. The balloon dissector assembly of claim 1, further including a guide assembly selectively engageable with the balloon dissector, the guide assembly including a housing and the guide member extending from the housing.

3. The balloon dissector assembly of claim 2, wherein the housing of the guide assembly is configured for snap-fit engagement with the handle of the balloon dissector.

4. The balloon dissector assembly of claim 1, wherein the dissection balloon includes a first length when the dissection balloon is in the deflated condition and a second length when the dissection balloon is in the inflated condition, the second length being greater than the first length.

5. The balloon dissector assembly of claim 1, wherein the handle of the balloon dissector includes an inflation port.

6. The balloon dissector assembly of claim 1, wherein the dissection balloon is transparent.

7. A dissector assembly comprising:
    the balloon dissector assembly of claim 1; and
    an access assembly configured to releasably receive the balloon dissector assembly.

8. The balloon dissector assembly of claim 1, wherein the dissection balloon is releasably secured to the guide member along a length of the guide member.

9. The balloon dissector assembly of claim 8, wherein an adhesive releasably secures the dissecting balloon to the guide member and is configured to permit the progressive inflation of the dissection balloon from the proximal end to the distal end.

10. A method for separating tissue, the method comprising:
    directing a dissection balloon through tissue of a patient to a first position within the patient, the dissection balloon having a deflated condition in which the dissection balloon extends distally from a distal portion of an elongate shaft and including a guide member received within and extending a length of the dissection balloon when the dissection balloon is in the deflated condition, the dissection balloon having proximal and distal portions and defining a longitudinal axis; and providing inflation fluid to the dissection balloon to inflate the dissection balloon progressively along the longitudinal axis of the dissection balloon from a proximal end of the dissection balloon to a distal end of the dissection balloon.

11. The method of claim 10, further including redirecting the dissection balloon to a second position within the patient while providing inflation fluid to the dissection balloon.

12. A balloon dissector assembly comprising:
a balloon dissector including,
an elongate shaft having a proximal portion and a distal portion and defining a longitudinal axis,
a guide member extending through the elongate shaft,
a handle disposed on the proximal portion of the elongate shaft, and
a dissection balloon supported on the distal portion of the elongate shaft and about the guide member, the dissection balloon having proximal and distal ends, the dissection balloon including a substantially cylindrical shape having a deflated condition in which the dissection balloon extends distally from the distal portion of the elongate shaft and includes a first diameter between the proximal and distal ends, an inflated condition in which the dissection balloon includes a second diameter between the proximal and distal ends, and a plurality of intermediate conditions in which the dissection balloon transitions from the deflated condition to the inflated condition progressively along a length of the dissection balloon from the proximal end to the distal end.

13. The balloon dissector assembly of claim 12, further including a guide assembly selectively engageable with the balloon dissector, the guide assembly including a housing and the guide member extending from the housing.

14. The balloon dissector assembly of claim 13, wherein the housing of the guide assembly is configured for snap-fit engagement with the handle of the balloon dissector.

15. The balloon dissector assembly of claim 12, wherein the dissection balloon includes a first length when the dissection balloon is in the deflated condition and a second length when the dissection balloon is in the inflated condition, the second length being greater than the first length.

16. The balloon dissector assembly of claim 12, wherein the handle of the balloon dissector includes an inflation port.

17. The balloon dissector assembly of claim 12, wherein the dissection balloon is transparent.

18. A dissector assembly comprising:
the balloon dissector assembly of claim 12; and
an access assembly configured to releasably receive the balloon dissector assembly.

19. The balloon dissector assembly of claim 12, wherein the dissection balloon is secured to the guide member along a length of the guide member with an adhesive.

* * * * *